United States Patent
Kaali et al.

[11] Patent Number: 5,185,086
[45] Date of Patent: Feb. 9, 1993

[54] METHOD AND SYSTEM FOR TREATMENT OF BLOOD AND/OR OTHER BODY FLUIDS AND/OR SYNTHETIC FLUIDS USING COMBINED FILTER ELEMENTS AND ELECTRIC FIELD FORCES

[76] Inventors: Steven Kaali, 88 Ashford Ave., Dobbs Ferry, N.Y. 10522; Peter M. Schwolsky, 20 Haslet Ave., Princeton, N.J. 08540

[21] Appl. No.: 730,690

[22] Filed: Jul. 16, 1991

[51] Int. Cl.$^5$ .................. B01D 35/06; B01D 37/00; A61K 41/00

[52] U.S. Cl. .................. 210/748; 55/487; 128/419 R; 128/421; 128/783; 204/131; 204/164; 204/186; 204/302; 210/243; 210/251; 210/314; 210/335; 210/416.1; 210/472; 210/634; 422/22; 422/44; 422/101

[58] Field of Search .......... 210/748, 764, 767, 243, 210/500.1, 498, 251, 314, 335, 641, 645, 650, 651, 634, 472, 258, 416.1; 55/483, 488; 128/419 R, 421, 783, 784; 604/4; 422/22, 44, 101; 204/131, 186, 164, 242, 275, 302, 305, 264, 276, 235

[56] References Cited

U.S. PATENT DOCUMENTS

| | | |
|---|---|---|
| 2,428,328 | 9/1947 | Ham et al. .................. 204/186 |
| 3,398,082 | 8/1968 | Lochmann et al. ............. 204/302 |
| 3,753,886 | 8/1973 | Myers ...................... 204/186 |
| 3,980,541 | 9/1976 | Aine ....................... 204/302 |
| 4,303,530 | 12/1981 | Shah et al. ................ 210/489 |
| 4,473,449 | 9/1984 | Michaels et al. ............ 210/748 |
| 4,594,138 | 6/1986 | Thompson ................... 204/302 |
| 4,751,003 | 6/1988 | Raehse et al. .............. 210/641 |
| 4,800,011 | 1/1989 | Abbott et al. .............. 210/748 |
| 5,076,933 | 12/1991 | Glenn et al. ............... 210/335 |
| 5,085,773 | 2/1992 | Danowski ................... 210/243 |
| 5,133,352 | 7/1992 | Lathrop et al. ............. 128/419 R |
| 5,139,684 | 8/1992 | Kaali et al. ............... 210/243 |

Primary Examiner—Robert A. Dawson
Assistant Examiner—Sun Uk Kim
Attorney, Agent, or Firm—Charles W. Helzer

[57] ABSTRACT

A method and system for the treatment of blood and/or other body fluids (such as amniotic fluids) as well as synthetic fluids such as tissue culture medium whereby a fluid to be treated is mechanically filtered for elimination of particles contained therein which exceed 0.2 microns in size (or some other minutely small size) and in addition subjecting the fluid being treated to electric field forces in the microwatt/milliwatt region induced by relatively low voltage of a few volts and low current density which does not exceed values which could impair the biological usefulness and characteristics of the blood or other fluid being treated.

19 Claims, 1 Drawing Sheet

METHOD AND SYSTEM FOR TREATMENT OF BLOOD AND/OR OTHER BODY FLUIDS AND/OR SYNTHETIC FLUIDS USING COMBINED FILTER ELEMENTS AND ELECTRIC FIELD FORCES

TECHNICAL FIELD

This invention relates to a novel combined filter and electrical field force method and system employing mechanical filtering in combination with the use of electric field forces to eliminate larger size particles entrained in fluids which are larger than 0.2 microns in size, and successively or simultaneously subject the fluid to electric field forces to attenuate virus, bacteria, parasites or fungus entrained in fluids such as blood or other body fluids and/or synthetic fluids such as tissue culture medium.

BACKGROUND OF THE INVENTION

U.S. patent applications Ser. No. 07/615,800, filed Nov. 16, 1990, now issued U.S. Pat. No. 5,139,684, entitled "Electrically Conductive Methods and Systems for Treatment of Blood and/or Other Body Fluids and/or Synthetic Fluids With Electric Forces"—Steven Kaali and Peter M. Schwolsky, Inventors, discloses novel electrically conductive methods and systems for transferring blood and/or other body fluids (such as amniotic fluids), and/or synthetic fluids such as tissue culture medium, from a donor to a transfusion recipient or storage receptacle, or vice versa, or for recirculating a single donor's blood or other body fluids through components of a treatment system external of the body or by implant devices for purging such contaminants. This treatment uses a novel low voltage, low current electrically operated vessel for direct electric treatment of blood and/or other body fluids, and/or synthetic fluids with electric field forces of appropriate field strength to attenuate contaminants such as bacteria, virus, fungus or parasites contained in the blood and/or other body fluid and/or synthetic fluids, and thereby render such contaminants and/or fluids ineffective to infect or affect normally healthy human cells. "Attenuate" means to reduce the infectivity of the blood, other body fluids, and/or synthetic fluids such as tissue culture medium being treated. The attenuation is believed to be achieved either by the direct and/or indirect physical effect of the electricity on the virus, bacteria, parasites and/or fungus, and/or the removal of such contaminants from the fluid being treated. The treatment, however, does not damage the fluid or render blood or other body fluid biologically unfit for use in humans or other mammals after the treatment. The treatment can be achieved with electric field forces during normally occurring transfer processing from a donor to a recipient or collection receptacle, or vice versa, or during recirculation of a single donor's blood or other body fluids, and/or synthetic fluids. A similar method and system using alternating current voltage and current is described in U.S. patent application Ser. No. 07/615,437 filed on Nov. 16, 1990 concurrently with the above-described U.S. patent application Ser. No. 07/615,800 now issued U.S. Pat. No. 5,139,684. The disclosures of both these applications hereby are incorporated into the disclosure of this application in their entirety.

The above-described novel method and system originally disclosed in the above-noted pending U.S. patent applications did not, however, include within its disclosure appropriate and efficient means for screening out larger particles that might be entrained in the fluid being treated which are larger than 0.2 microns in size, prior to treatment. To overcome this deficiency, the present invention was devised.

SUMMARY OF THE INVENTION

It is therefore a principle object of this invention to provide an improved method and system for treating blood and/or other body fluids (such as amniotic fluids) of mammals as well as synthetic fluids. The improved method and system comprises subjecting a fluid to be treated to mechanical filtering for elimination of any particles contained therein which exceed 0.2 microns in size and additionally subjecting the fluid being treated to electric field forces in the microwatt/milliwatt region induced by a relatively low voltage of a few volts and low current densities of from about 1 microampere per square millimeter to about a few milliamperes per square millimeter which does not exceed a value that could impair the biological quality and characteristics of blood or other fluids being treated. The mechanical filtering preferably takes place serially in stages whereby increasingly smaller size particles are serially filtered out by mechanical filter means. The treatment with electric field forces preferably is done concurrently with the mechanical filtering, but alternatively may be done sequentially following and/or before the filtering.

BRIEF DESCRIPTION OF DRAWINGS

These and other objects, features and many of the attendant advantages of this invention will be appreciated more readily as the same becomes better understood from a reading of the following detailed description when considered in connection with the accompanying drawings, wherein like parts in each of the several figures are identified by the same reference characters, and wherein.

BEST MODE OF PRACTICING THE INVENTION

Figure 1:
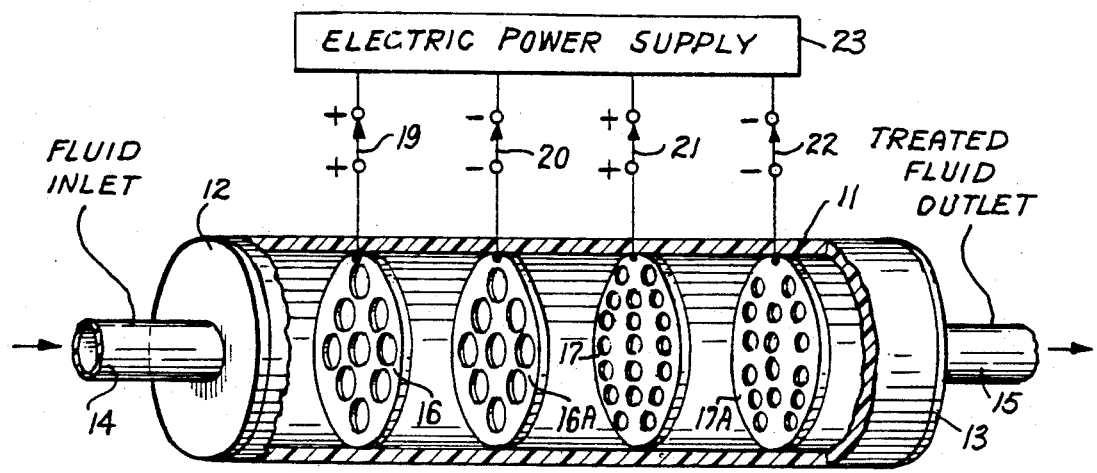
FIG. 1 is a partial schematic view of a new and improved combined mechanical filter and electric field force treatment system and apparatus according to the invention.

FIG. 1 is a partial schematic drawing of a novel filtration and electrical treatment method and system according to the invention. In FIG. 1 a plastic or other closed, electrically insulating, treatment vessel 11 is provided which has an elongated cylindrical shape with both ends closed as shown at 12 and 13. The ends 12 and 13 are provided with inlet and outlet openings through pipes 14 and 15, respectively. Secured within the hollow interior of cylindrical vessel 11 are a series of filter plate elements 16, 16A, 17 and 17A. The filter plate elements preferably are fabricated from an electrically conductive material such as platinum which is substantially chemically inert and does not chemically react with blood or other human body fluid or synthetic fluids such as tissue culture medium. Each of the filter plate elements 16 and 16A have a plurality of aperture openings formed therein, which may or may not be axially aligned with respect to each other, but are of a given size for screening out and blocking particles contained in fluids being filtered which are in excess of the given size. For example, filter plate elements 16 and 16A may serve to filter out particles having a cross sectional dimension which is equal to or greater than 4 microns in size.

Downstream in the liquid flow path through vessel 11, a second set of filter plate elements 17, 17A are supported. The filter plate elements 17, 17A likewise are fabricated from a suitable electrically conductive material such as platinum and have sets of aperture openings formed therethrough which may or may not be axially aligned with respect to each other. The aperture openings in the filter plate elements 17 and 17A however are smaller and more numerous than the openings in filter plates elements 16 and 16A. For example, the aperture openings in the filter plate elements 17, 17A may be sized to block or filter out particles having a size either equal to or in excess of 0.2 microns in size up to 4 microns in size. While only two different size sets of filter plate elements have been illustrated, it is believed obvious to those skilled in the art that additional, differently sized filter plate elements may be included within the vessel 11 depending upon the nature of the particles which one desires to filter out from fluid being treated with the system. The filter plate elements 16, 16A and 17, 17A are mounted within the interior of hollow, cylindrical vessel 11 substantially at right angles to the flow path that extends longitudinally through vessel 11 from inlet end 12 to and through outlet end 13. The mounting of the filter plate elements is such that each filter element is electrically insulated from the other filter plate elements mounted within vessel 11.

In operation, fluid to be filtered is supplied to the inlet end 12 of insulated vessel 11 via inlet conduit 14 and traverses past the filter element plates 16, 16A, 17 and 17A then exits through the fluid outlet conduit 15. At the exit side all particles entrained in the fluid which are larger than 0.2 microns in size will have been filtered out.

Concurrently with the above-described filtering action, a low value electrical potential of the order from about 0.2 to about 12 volts is supplied to respective ones of the filter element plates 16, 16A, 17 and 17A from a direct current power source 23 via selector switches 19, 20, 21 and 22. Switches 19, 20, 21 and 22 serve to electrically connect respective ones of the filter plate elements to alternate polarity output electric potentials supplied from the direct current electric power supply 23. The electric potential supplied to respective ones of the filter plate elements 16, 16A and 17, 17A may vary in magnitude from about 0.2 to about 12 volts, for example, but are of opposite polarity relative to adjacent filter plate elements. For example, assume that a direct current electrical excitation voltage having positive (+) polarity and a value of 4 volts is supplied to the filter plate element 16. Then a negative (−) 4 volts or any other of the above-noted values is supplied to the neighboring filter plate element 16A. Consequently, there will be a potential difference of 8 volts between the adjacent filter plate elements 16 and 16A through which the fluid being treated must pass. If desired, the potential difference existing between the next adjacent pairs of plates 17, 17A may be adjusted either to higher or to lower values in order to adjust the strength of the electric field between the stages of filtration to a desired value.

In operation, the system functions in the same manner as was described more fully in the above-noted copending U.S. application Ser. No. 07/615,800 now issued U.S. Pat. No. 5,139,684, the disclosure of which has been incorporated into the disclosure of this application in its entirety. In effect, the electrical treatment attenuates any virus, bacteria, fungus and/or parasite so as to render them ineffective to infect normally healthy cells while maintaining the biological usefulness of blood, and/or other body fluids, and/or synthetic fluids being treated. During operation, the low voltage electric potentials applied to the respective filter plate elements should be of the order from about 0.2 to about 12 volts and should produce current flow through the fluid in current densities ranging from about 1 microampere per square millimeter of filter plate element area exposed to fluid being treated to about 1 milliampere per square millimeter with direct current excitation to about 2 milliamperes per square millimeter using alternating current excitation. Treatment time within this range of parameters may extend for a period of from about 1 minute to about 12 minutes during electrification. However, treatment time may be longer where, in certain cases, more complete attenuation of the contaminants in the fluid being treated is desired. Also, in certain circumstances where faster attenuation of contaminants is desired, the excitation voltage may exceed the 0.2 to about 12 volt range indicated for most treatments.

During operation of the method and system described with relation to the system described in the above-noted U.S. patent application Ser. No. 07/615,800 now issued U.S. Pat. No. 5,139,684, it has been observed that under certain conditions bubbling of gas around one or more of the plate elements such as 16, 16A, 17 or 17A can occur. To avoid any adverse effects on the fluids being treated, it is possible to reduce or even eliminate the production of bubbles at the plate elements during operation by a number of techniques. One is to fill the treatment vessel 11 so completely that a gas phase cannot develop above the liquid in the vessel.

Figure 2:
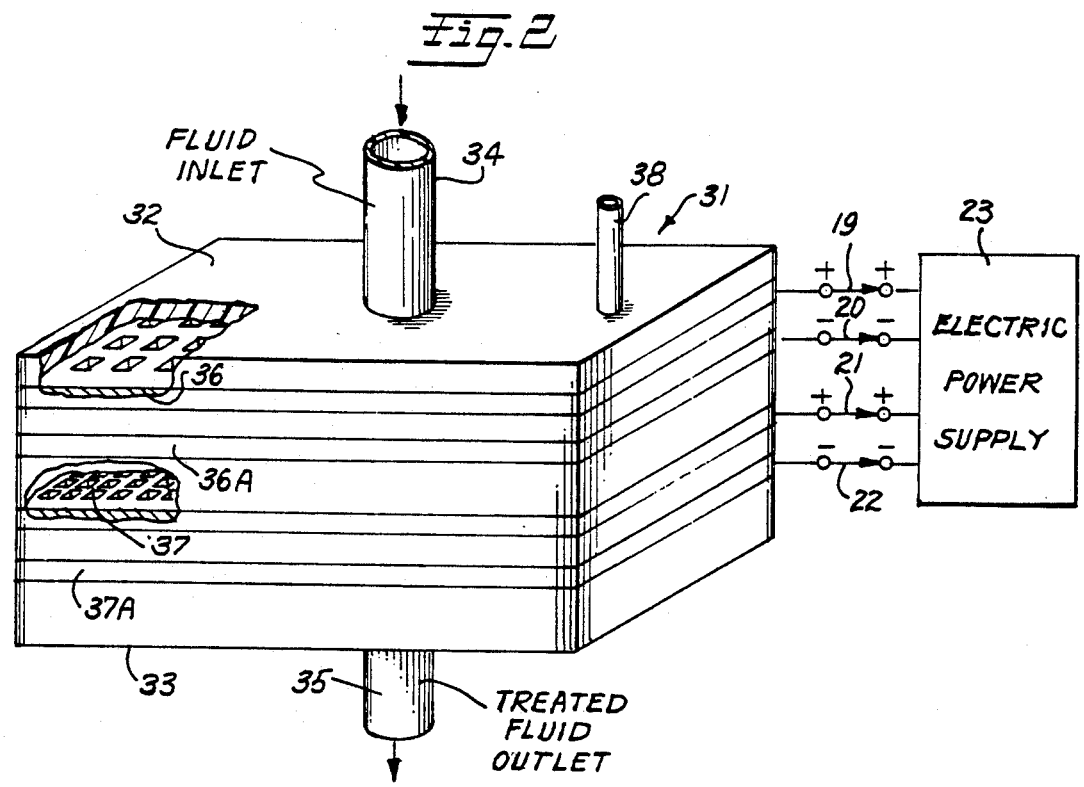
FIG. 2 is a schematic view of an alternative form of system and apparatus according to the invention.

Another technique that can be used to avoid bubbling at the plates is to provide a suitable vent pipe such as shown at 38 in the embodiment of the invention shown in FIG. 2 of the drawings. By introducing pressurized air or a suitable inert gas that does not chemically react with the fluids being treated, the liquid can be pressurized to the point that the liquid will not pass into the gas phase. Another alternative is to vent any gas produced by bubbling to the atmosphere via a vent tube such as 38 shown in FIG. 2. Other techniques for obviating the bubbling around the filter plate elements will be suggested to those skilled in the art.

During operation of the filter elements 16, 16A, 17, 17A it is possible that one or more of the filter elements can become clogged either partially or otherwise. In this eventuality the system can be shut down and the clogged element replaced with a new clean filter element. Alternatively, it is possible to design the system so as to provide two parallel treatment paths together with suitable valve means to selectively supply fluid being treated to one treatment path or the other. With such an arrangement it would not be necessary to shut the system down during operation to remove and replace a clogged filter plate element.

FIG. 2 is a partial perspective view of a second embodiment of the invention which employs a generally rectangular, box-like treatment vessel 31 fabricated from plastic or other electrical insulating material closed by an insulating top 32 and an insulating bottom 33. A fluid inlet conduit 34 is provided in top 32 and an outlet conduit 35 is provided in bottom 33. The near sides and top of vessel 31 have been broken away to show the construction of the mechanical filter elements 36, 36A and 37, 37A all of which are fabricated from platinum or other relatively inert electrically conductive material which is compatible with human blood, and/or body fluids, and/or synthetic fluids, and/or tissue. As shown in FIG. 2, the upper set of filter plate elements 36 and 36A are relatively coarse compared to the lower set of filter plate elements 37 and 37A. Again, for example, the upper filter plate pair 36, 36A may be designed to prevent particles which are 4 microns or larger in cross section from passing through the elements while the lower set of elements 37, 37A may be designed to prevent the passage of particles 0.2 microns or larger from passing through. Again, as a matter of design, the passages through the sets of filter plates elements 36, 36A and 37, 37A may be axially aligned or relatively displaced from each other so as to form a more tortuous path for fluid flowing downwardly from the fluid inlet 34 to the discharge outlet 35.

An electric power supply 23 is provided which may be either direct current or alternating current so long that measures are taken to assure that the electric potential supplied to the respective filter plate elements 36, 36A and 37, 37A are out of phase relative to each other to assure that a potential difference exists between adjacent pairs of the filter elements as described with relation to FIG. 1.

In operation, the embodiment of the invention shown in FIG. 2 functions in substantially the same manner as that shown in FIG. 1 to provide for mechanical filtering out of particles entrained in fluid to be treated by the system which are greater than 0.2 microns in size. Concurrently, electrification of the filter plate elements in the manner described with relation to FIG. 1 causes attenuation of virus, bacteria, fungus, and/or parasites which might be entrained in the fluid being treated by the system thereby rendering them ineffective as described more fully in the above-referenced co-pending U.S. patent applications.

If necessary, anticoagulants may be used in the fluids being treated with either embodiment of the invention shown in FIG. 1 or FIG. 2.

INDUSTRIAL APPLICABILITY

The present invention provides a combined filtration-electrical treatment method and system which in operation serves to attenuate virus, bacteria, fungus and/or parasites found in blood, body fluids and/or synthetic fluids (such as tissue culture medium) used in the production and purification of biologicals. The system is designed such that no damage or impairment of the biological usefulness of the fluids being treated occurs as a result of the combined filtration and electrification treatments.

Having described two embodiments of a novel combined filtration and electrification treatment method and system according to the invention, other modifications and variations of the invention will be suggested to those skilled in the art in the light of the above teachings. It is therefor to be understood that changes may be made in the particular embodiments of the invention described which are within the full intended scope of the invention as defined by the appended claims.

What is claimed is:

1. The method of treating blood and/or other body fluids of mammals as well as synthetic fluids which comprises subjecting a fluid to be treated to filtering for elimination of any particles contained therein which exceed 0.2 microns in size and subjecting the fluid while being filtered to electric field forces between spaced-apart electrodes in the microwatt/milliwatt region induced by a relatively low voltage of about 0.2 to 12 volts and low current density of about 1 microampere per square millimeter to about 2 milliamperes per square millimeter of electrode area which does not exceed a value that impairs the biological characteristics of the blood or other fluid being treated.

2. The method according to claim 1 wherein the filtering and electrification of the fluid being tested are done concurrently.

3. The method according to claim 1 wherein a first stage of filtering removes all particles entrained in the fluid which are in excess of about 4 microns in size and a second stage of filtering removes all particles in the fluid which exceed 0.2 microns up to about 4 microns in size.

4. The method according to claim 1 further including pressurizing and/or venting the fluid being treated during treatment.

5. The method according to claim 1 wherein direct current voltage and current are used to produce the electric field forces and wherein the low voltage is in the range from about 0.2 volts to about 12 volts and induces electric current densities in the fluid of from about 1 microampere per square millimeter to about 1 milliampere per square millimeter.

6. The method according to claim 1 wherein alternating current voltage and current are used to produce the electric field forces and wherein the low voltage is in the range from about 0.2 volts to about 12 volts and induces electric current flow densities in the fluid of from about 1 microampere per square millimeter to about 2 milliamperes per square millimeter.

7. The method according to claim 1 wherein the filtering takes place serially in stages whereby increasingly smaller size particles are serially filtered out mechanically.

8. The method according to claim 7 wherein the filtering and electrification are done concurrently.

9. The method according to claim 8 wherein a first stage of filtering removes all particles entrained in the fluid which are in excess of about 4 microns in size and a second stage of filtering removes all particles in the fluid which exceed 0.2 microns up to about 4 microns in size.

10. The method according to claim 9 further including pressurizing and/or venting the fluid being treated during treatment.

11. A system for the treatment of blood and/or other body fluids of mammals as well as synthetic fluids which comprises filter means for subjecting a fluid to be treated to filtering for elimination of any particles contained therein which exceed about 4 microns in size and fluid electrification means for subjecting the fluid while being filtered to electric field forces between spaced-apart electrodes in the microwatt/milliwatt region by application of an electric field force of relatively low voltage of about 0.2 to 12 volts between the electrodes across the fluid for inducing a low current density flow of from about 1 microampere to 2 milliamperes per square millimeter of electrode area therethrough and which does not exceed a value that impairs the biological usefulness of the fluid.

12. The system of claim 11 wherein the filter means is a multi-stage filter whereby increasingly smaller size particles are filtered out from the fluid as it proceeds through the filter.

13. The system of claim 12 wherein the filter means precedes the fluid electrification means.

14. The system of claim 12 wherein the filter means and the fluid electrification means are comprised by the same elements that perform both the function of filtering and the function of electrification in a single apparatus.

15. The system according to claim 14 wherein the filter means comprises a first filter stage which removes all particles entrained in the fluid which are 4 microns in size or larger followed by a second stage filter which removes all particles in the fluid that are 0.2 microns up to about 4 microns in size.

16. The system according to claim 15 wherein the electric field force means uses direct current voltage and current and wherein the low voltage is in the range of from about 0.2 volts to about 12 volts and induces electric current flow densities of from about 1 microampere per square millimeter to about 1 milliampere per square millimeter.

17. The system according to claim 16 wherein means for pressurizing and/or venting fluid being treated are provided.

18. The system according to claim 15 wherein the electric field force means uses alternating current voltage and current and wherein the low voltage is in the range from about 0.2 volts to about 12 volts and induces a current flow density of from about 1 microampere per square millimeter to about 2 milliamperes per square millimeter.

19. The system according to claim 18 wherein means for pressurizing and/or venting fluid being treated are provided.

* * * * *